United States Patent
Jones et al.

(10) Patent No.: US 6,784,168 B1
(45) Date of Patent: Aug. 31, 2004

(54) BIOCIDAL COMPOSITIONS AND TREATMENTS

(75) Inventors: Christopher Raymond Jones, West Midlands (GB); Robert Eric Talbot, Staffordshire (GB)

(73) Assignee: Rhodia Consumer Specialties Limited, Oldbury (GB)

(*) Notice: Subject to any disclaimer, the term of this patent is extended or adjusted under 35 U.S.C. 154(b) by 0 days.

(21) Appl. No.: 09/582,152

(22) PCT Filed: Dec. 21, 1998

(86) PCT No.: PCT/EP98/08394

§ 371 (c)(1),
(2), (4) Date: Sep. 5, 2000

(87) PCT Pub. No.: WO99/33345

PCT Pub. Date: Jul. 8, 1999

(30) Foreign Application Priority Data

| Dec. 23, 1997 | (GB) | ................................................ 9727006 |
| Mar. 14, 1998 | (GB) | ................................................ 9805407 |
| Mar. 19, 1998 | (GB) | ................................................ 9805746 |
| Jun. 3, 1998 | (GB) | ................................................ 9811778 |
| Sep. 18, 1998 | (GB) | ................................................ 9820255 |

(51) Int. Cl.$^7$ ........................ A01N 57/26; A01N 57/00
(52) U.S. Cl. ........................ 514/76; 514/104; 514/107; 514/108; 514/114; 514/136
(58) Field of Search .................... 514/76, 104, 107, 514/108, 114, 136

(56) References Cited

U.S. PATENT DOCUMENTS

| 3,644,083 A | | 2/1972 | Frederick et al. |
| 4,599,372 A | * | 7/1986 | Bardoliwalla et al. |
| 4,602,011 A | * | 7/1986 | West et al. |

FOREIGN PATENT DOCUMENTS

| EP | 0 385 676 A | | 9/1990 |
| EP | 0491 391 | * | 6/1992 |
| GB | 2 145 708 | * | 4/1985 |
| GB | 2 178 960 A | | 2/1987 |
| GB | 2 257 043 A | | 6/1993 |
| WO | 91 04668 A | | 4/1991 |
| WO | 96/14092 | * | 5/1996 |

* cited by examiner

Primary Examiner—Sreeni Padmanabhan
Assistant Examiner—San-ming Hui
(74) Attorney, Agent, or Firm—Frishauf, Holtz, Goodman & Chick, P.C.

(57) ABSTRACT

A synergistic biocide comprises a tris(hydroxymethyl) phosphine or a tetrakis (hydroxymethyl)phosphonium salt and at least one non-surfactant biopenetrant, such as a polymer or copolymer having a plurality of quaternary ammonium groups, a hydrotrope or a syntan, together optionally with a surfactant.

6 Claims, No Drawings

BIOCIDAL COMPOSITIONS AND TREATMENTS

The present invention relates to synergistic biocidal mixtures of hydroxymethyl phosphonium biocides with certain non-foaming biopenetrants.

GB 2 145 708 describes biocidal uses of tetrakis (hydroxymethyl) phosphonium salts. which, together with their parent base, tris(hydroxymethyl)phosphine, are referred to herein collectively as "THP". U.S. Pat. No. 4,778,813 describes the biocidal use of quaternary ammonium polymers. GB 2 178 960 describes synergism between THP and surfactant. GB 2 228 680 describes synergism between THP and certain aldehydes.

THP formulations are increasingly widely used as biocides for water treatment in treating cooling water, process water e.g. in pulp and paper manufacture, drilling fluids and other aerobic water systems, as well as in anaerobic systems such as oil field formation water, injection water, produced water and water used in hydrostatic testing. Advantages include rapid and effective bactericidal activity and environmental acceptability. Particularly in systems where slime forming bacteria proliferate (e.g. in aerobic systems such as cooling water) it has been found desirable to use THP formulations containing synergistic amounts of a surfactant according to GB 2 178 960, in order to improve cost effective biocidal action. It is believed that the surfactant aids the penetration of the biomass by the THP. However such formulations cause foaming problems. Attempts to combine THP with other biocides (e.g. aldehydes), which do not cause foaming, have not been able to provide such effective biocidal action against slime forming bacteria, and/or have detracted from the favourable environmental profile of THP.

We have now discovered that combinations of THP with certain non-surfactant biopenetrants provide strongly synergistic biocidal formulations which give excellent penetration of bacterial slime and improved activity against planktonic bacteria without causing excessive foam. We have further discovered that mixtures of THP with a surfactant, and with a non-surfactant biopenetrant give a marked ternary synergism, permitting improved biocidal efficiency with reduced foaming.

Our invention provides a biocidally synergistic mixture comprising THP and at least one THP-compatible, non-surfactant, biopenetrant synergist together optionally with a surfactant The non-surfactant biopenetrant may be selected from quaternary ammonium polymers and copolymers, hydrotropes and syntans.

According to a second embodiment the invention provides a method of treating aqueous systems contaminated, or liable to contamination, with microbes such as bacteria. fungi or algae which comprises applying thereto separately or together a biocidally active amount of the components of a synergistic mixture as aforesaid.

The aqueous system may, for instance, be contaminated with bacterial slime and/or planktonic bacteria. The invention is of use for treating aerobic systems such as cooling towers and also for anaerobic systems, such as oil wells, e.g. during secondary recovery.

The THP is conveniently present in the formulation as a salt, but is preferably used at a pH sufficient to form the base. The salt is preferably the sulphate, chloride or phosphate. However any water soluble salt may be used including the phosphite, bromide, fluoride, carbonate, acetate, formate, citrate, borate, or silicate In fact any counter ion which is chemically compatible with THP may be used, the main criteria for selection being economic. Oxidation of THP to tris(hydroxymethyl)phosphine oxide (THPO) should be avoided and oxidising agents for THP are preferably substantially absent. The composition may contain oxygen scavengers to minimise oxidation by atmospheric oxygen. The pH of the composition may be below 3.5 to avoid THPO formation during storage but the pH on addition to aqueous systems is preferably between 3.5 and 9 and more preferably less than 8, e.g. 4 to 7.5. High alkalinity, e.g. above 10, is preferably avoided. The pH of the aqueous system may optionally be adjusted by addition of alkali or acid as appropriate.

An essential component of the invention is a non-surfactant biopenetrant. Surfactants are amphiphilic compounds which, even when present in low concentrations in water (e.g. 0.1% by weight), substantially reduce the interfacial free energy of a water/hydrophobe interface. Surfactants may be identified by their effect on surface tension of water. Non-surfactants do not appreciably reduce surface tension at low concentrations. Typically the reduction of surface tension by a non-surfactant at concentrations of the order of 0.1% does not amount to more than about 5% of the value for pure distilled water. At the same concentrations typical surfactants would reduce surface tension by 50% or more. For the purposes of this specification a compound is considered non-surfactant if it lowers the surface tension of water by less than 20% at a concentration of 0.1% by weight. Preferably the reduction is less than 15%, e.g. less than 10%, especially less than 5%.

The non-surfactant biopenetrant may for example be a quaternary ammonium polymer or copolymer. The quaternary ammonium polymer may for example be any of those described in U.S. Pat. No. 4,778,813. Particularly preferred is poly[oxyethylene(dimethyliminio)ethylene (dimethyliminio)ethylene dichloride]. This a copolymer of NNN'N'-tetramethyl-1,2-diamino ethane with bis (2-chloroethyl) ether, which is referred to herein as "WSCP". The latter is the commercial name of the product used in example 1, which is sold by Buckman Laboratories. However any other water soluble polymer containing a plurality of quaternary ammonium groups may be used. Such compounds typically comprise a polymeric cation of the formula:

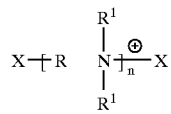

wherein: each R is a divalent organic group constituting with the ammonium group a monomeric residue or separately selected from two or more comonomeric residues; each $R^1$ is an alkyl or hydroxy alkyl group, typically having from 1 to 4 carbon atoms and preferably methyl or ethyl; X is hydrogen or a monovalent inorganic or organic end capping group; and n is from 2 to 3000, e.g. 5 to 2000, especially 8 to 1000, e.g. 10 to 500, most preferably 20 to 100. The counter ion may be any convenient THP-compatible anion e.g. chloride, sulphate, phosphate, bromide, fluoride, carbonate, formate, acetate, citrate, lactate, tartrate, methosulphate, borate or silicate.

R may for example be a $C_{1-6}$ alkylene, oxyalkylene, polyoxyalkylene, haloalkylene, halooxyalkylene, halopolyoxyakylene or a

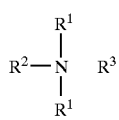

group wherein $R^2$ may be a $C_{1-6}$ alkylene, oxyalkylene polyoxyalkylene, haloalkylene, halooxyalkylene or halopolyoxyalkylene group and $R^3$ represents a covalent bond or an $R^2$ group. The polymer may for example be a methylated polyethylene polyamine of the formula

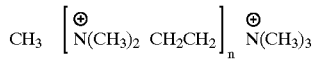

where n is 2 to 10.

Some other typical examples include:

Poly[hydroxyethylene(dimethyliminio)ethylene (dimethyliminio)methylene dichloride]
Poly[hydroxyethylene(dimethyliminio)-2-hydroxypropylene(dimethyliminio)-methylene dichloride]
N-[3-(dimethylammonio)propyl]-N[3-(ethyleneoxyethylenedimethylammonio) propyl]urea dichloride
-4-[1-tris(2-hydroxyethyl)ammonium chloride-2-butenyl] poly[1-dimethyl-ammonium chloride-2-butenyl]tris(2-hydroxyethyl)ammonium chloride The non-surfactant biopenetrant may alternatively be a hydrotrope. Hydrotropes are sometimes confused with surfactants because they are also amphiphilic. However hydrotropes do not significantly affect surface tension at low concentrations. Hydrotropes act as solubilisers. When present in relatively high concentrations (e.g. greater than about 1%) they increase the water solubility of sparingly or moderately soluble solutes.

A preferred class of hydrotropes includes water soluble glycol ethers. The glycol ether is preferably a water soluble compound of the formula $HO[CR_2CR_2O])_nR'$ where each R is methyl, ethyl or preferably H, provided that the total number of carbon atoms per $[CR_2CR_2O]$ group does not exceed 4, more preferably is not more than 3 and most preferably is 2, R' is a lower hydrocarbon group such that the compound is water soluble, e.g. butyl, propyl, ethyl or preferably methyl and n is from 1 to 20, preferably 1 to 10, especially 1 to 5, typically 1 to 3, most preferably 2. Preferred examples include diethylene glycol monomethyl ether.

An important class of hydrotropes for use according to our invention comprises the lower alkyl aryl sulphonates. Water soluble salts, e.g. sodium, potassium, ammonium or salts of benzene sulphonic, toluene sulphonic, xylene sulphonic, ethyl benzene sulphonic or cumene sulphonic acids are very effective. Generally, alkylbenzene sulphonic acids having up to four or even five aliphatic carbon atoms show hydrotropicity but not significant surfactancy. Above six aliphatic carbons, e.g. sodium octyl benzene sulphonate, surfactancy predominates over hydrotropicity. Naphthalene sulphonates are also useful as non-surfactant biopenetrants, e.g. alkali metal $C_{1-4}$ alkyl naphthalene sulphonates. Urea is also an effective hydrotrope.

A further category of non-surfactant biopenetrants comprises syntans. The latter include a variety of resins and prepolymers which are used in the tanning industry as an alternative to tannin or chrome.

Animal skins comprise a layer of collagen, and tanning agents react to cross link reactive sites within the collagen. One effect of this reaction is to increase the minimum temperature at which the leather tends to shrink in hot water.

For the purpose of this specification "syntan" is used to refer to synthetic organic compounds capable of reacting with collagen to form cross links so as to increase the shrink temperature of leather. For example the term includes any water soluble polymer prepared by copolymerising formaldehyde, which is capable of increasing the shrink resistance of collagen and which comprises at least two units of the formula

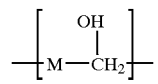

where each M is an aryl group such as a phenyl, naphthyl or aniline group substituted with one or more hydroxyl and/or sulphate, sulphone or sulphonimide groups or a nitrogenous comonomer such as a dicyandiamide, urea or melamine residue. As used herein the term "syntan" also includes resin syntans which are homopolyrners and copolymers of unsaturated carboxylic acids or their salts. esters, amides or nitrites, e.g. acrylic acid, methacrylic acid, acrylamide, acrylonitrile, maleic acid, fumaric acid, itaconic acid, aconitic acid, crotonic acid, isocrotonic acid, citraconic acid, mesaconic acid, angelic acid, tiglic acid and cinnamic acid. The copolymers may also comprise other vinylic comonomers such as styrene. Also included are acetone condensates with, for example sulphones and sulphonamides, and dicyandiamide based resins. Particularly preferred are: sulphonated aryl formaldehyde copolymers; condensates of THP with nitrogen compounds; phosphono polyacrylate or maleate telomers such as those described in EP 0 491 391; or phosphono ethyl phosphino telomers as described in EP 0 861 846.

The sulphonated aryl formaldehyde copolymer may for example be sodium naphthalene sulphonate formaldehyde condensate, sodium phenol formaldehyde concentrate, or sodium resorcinol formaldehyde condensate, or a condensate of formaldehyde with a sodium alkyl benzene or naphthalene sulphonate having less than 5 carbon atoms.

THP condensates may contain 2 or more phosphorus atoms, so long as the phosphorus compound is water soluble to a concentration of at least 0.5 g/l at 25° C. Such phosphorus compounds contain a total of at least 2 hydroxymethyl groups, usually at least one per phosphorus atom, and preferably at least 2 hydroxymethyl groups per phosphorus atom. The group or groups joining the phosphorus atoms together may be of the formula —R—, —R—O—, —R—O—R—, —R—NH—R or —R—R"—R— where R is an alkylene group of 1 to 4 carbon atoms and R" is the residue formed by removal of two hydrogen atoms, bonded to nitrogen, from a di or polyamide or an amine or di or polyamine, such as urea, a $C_{1-20}$alkylamine, dicyandiamide, thiourea or guanidine. Such compounds with 2 or more, e.g. 3, hydroxyalkyl groups per phosphorus atom may be made by self condensation of THP salts with a compound of general formula $R''H_2$ such as urea, or a $C_{1\ to\ 20}$alkylamine, e.g. by heating at 40 to 120° C.

The THP condensate may be prepared in situ by adding THP and a minor proportion of (for example) a condensable comonomer such as urea, melamine, an amine or dicyandiamide, simultaneously or consecutively to the system to be treated. Thus, for example, urea or aryl sulphonate hydrotrope may function as hydrotropes or comonomers for the in situ formation of syntans or in both capacities, in accordance with our invention.

The phosphono telomer may be a compound of the formula

wherein at least one R group in each unit is a COOM, CH$_2$OH, sulphono or phosphono group and the other r group which may be the same as, or different from, the first R group, is hydrogen or a COOM, hydroxyl, phosphono, sulphono, sulphate and/or hydroxy substituted C$_{1-7}$ alkyl or C$_{1-7}$ alkenyl group, and each M is a cation such that the phosphonated oligomer is water soluble and n is greater than 1, e.g. up to 10.

It is possible to use cotelomers, e.g. of the above formula, but in which the [CHRCHR]n chain contains at least two [CHRCHR] groups derived from different monomers and in which n has a total value of at least 3. For example we include a phosphonated trimer or higher cooligomer of maleate and acrylate containing at least one [CH$_2$ CHCOOM] and at least one [CHCOOM CHCOOM] group.

Particularly preferred are phosphonated oligomers of maleic acid, of the formula H(CHCO$_2$M.CHCO$_2$M)$_a$PO$_3$M$_2$ where n is greater than 1 and M is a cationic species such that the compound is water soluble, and especially mixtures of such compounds with phosphonosuccinic acid or its water soluble salts.

Particularly preferred are mixtures of phosphonosuccinate salts and an oligomer of the above formula when n=2, such as may be prepared by reacting sodium phosphite with a small molar excess of sodium maleate in a concentrated alkaline aqueous solution at elevated temperatures in the presence of a free radical source such as hydrogen peroxide.

Other phosphono telomers which are used according to the invention include phosphono acrylate telomers, e.g. of the formula:

where n may be 2 to 60, preferably 3 to 30, e.g. 4 to 20.

1-Phosphono-2-phosphino ethane can be reacted with salts of telomerisable unsaturated acids such as maleic and acrylic to make syntans which are useful in the present invention. Other phosphono carboxylates of use include phosphonosuccinates and salts of 2-phosphono-1,2,4-tricarboxy butane.

The biopenetrant synergist is not usually present in a greater weight concentration than the THP, although higher concentrations by weight based on THP, e.g. up to 10:1 or even 100:1 are technically possible but commercially undesirable. The proportion is preferably less than 50% by weight based on the weight of THP, more usually less than 20%, typically less than 10%, especially less than 5%. Although very small amounts may be effective we prefer to use proportions of biopenetrant greater than 0.1% based on the weight of THP, usually greater than 0.5%, especially greater than 1%.

The biocide is typically supplied as a 10 to 75%, e.g. 20 to 60%, especially 30 to 50% by weight aqueous solution of THP containing from 0.1 to 10% e.g. 0.2 to 5%, especially 0.5 to 2% of the synergist, based on the total weight of the solution.

Alternatively the composition may be supplied as a solid formed by coating THP onto, or absorbing it into, a powdery granular or porous acid substrate such as adipic acid.

The mixture is typically used at a dosage of 1 to 1500 ppm by weight THP based on the weight of water to be treated, usually 2 to 500, especially 5 to 250, e.g. 10 to 150.

According to a particular embodiment it has been found that mixtures of the aforesaid biopenetrant synergists with surfactants and THP salts provide an enhanced synergism. Such mixtures can provide even more effective biocidal activity, at substantially lower levels of both biocide and surfactant than arm required for conventional mixtures of THP salts and surfactant.

Our invention accordingly further provides a biocidally synergistic mixture comprising: (A) THP; (B) at )cast one non-surfactant biopenetrant; and (C) a surfactant.

The invention further provides a method of treating water with a biocidally active amount of said synergistic mixture.

Surfactants for use in our invention typically contain hydrophobic groups such as alkenyl, cycloalkenyl, alkyl, cycloalkyl, aryl, alkyl/aryl or more complex aryl (as in petroleum sulphonates) moieties having from 8 to 22, preferably 10 to 20, typically 12 to 18 carbon atoms and a hydrophilic moiety. Other hydrophobic groups included in the invention are polysiloxane groups.

The surfactant may for example consist substantially of an at least sparingly water-soluble salt of sulphonic or mono esterified sulphuric acids, e.g. an alkylbenzene sulphonate, alkyl sulphate, alkyl ether sulphate, olefin sulphonate, alkane sulphonate, alkylphenol sulphate, alkylphenol ether sulphate, alkylethanolamide sulphate, alkylethanolamide-ther sulphate, or alpha sulpho fatty acid or its ester each having at least one alkyl or alkenyl group with from 8 to 22, more usually 10 to 20, aliphatic carbons atoms.

The expression "ether" hereinbefore refers to compounds containing one or more glyceryl groups and/or an oxyalkylene or polyoxyalkylene group especially a group containing from 1 to 20 oxyethylene and/or oxypropylene groups. One or more oxybutylene groups may additionally or alternatively be present. For example, the sulphonated or sulphated surfactant may be sodium dodecyl benzene sulphonate, potassium hexadecyl benzene sulphonate, sodium dodecyl dimethyl benzene sulphonate, sodium lauryl sulphate, sodium tallow sulphate, potassium oleyl sulphate, ammonium lauryl monoethoxy sulphate, or monoethanolamine cetyl 10 mole ethoxylate sulphate.

Other anionic surfactants useful according to the present invention include alkyl sulphosuccinates, such as sodium di-2-ethylhexylsulphosuccinate and sodium dihexylsulphosuccinate, alkyl ether sulphosuccinates, alkyl sulphosuccinamates, alkyl ether sulphosuccinomates, acyl sarcosinates, acyl taurides, isethionates, soaps such as stearates, palmitates, resinates, oleates, linoleates, and alkyl ether carboxylates. Anionic phosphate esters and alkyl phosphonates, alkyl amino and imino methylene phosphonates may also be used. In each case the anionic surfactant typically contains at least one aliphatic hydrocarbon chain having from 8 to 22, preferably 10 to 20 carbon atoms, and, in the case of ethers, one or more glyceryl and/or from 1 to 20 oxyethylene and/or oxypropylene and/or oxybutylene groups.

Preferred anionic surfactants are sodium salts. Other salts of commercial interest include those of potassium, lithium, calcium, magnesium, ammonium, monoethanolamine, diethanolamine, triethanolamine, alkyl amines containing up to seven aliphatic carbon atoms, and alkyl and/or hydroxyalkyl phosphonium.

The surfactant may optionally contain or consist of nonionic surfactants. The nonionic surfactant may be, e.g. a C$_{10-22}$ alkanolamide of a mono or di- lower alkanolamine, such a coconut monoethanolamide. Other nonionic surfactants which may optionally be present, include tertiary acetylenic glycols, polyethoxylated alcohols, polyethoxylated mercaptans, polyethoxylated carboxylic acids, polyethoxylated amines, polyethoxylated alkylolamides, polyethoxylated alkylphenols, polyethoxylated glyceryl esters, polyethoxylated sorbitan esters, polyethoxylated phosphate esters, and the propoxylated or ethoxylated and propoxylated analogues of all the aforesaid ethoxylated nonionics, all having a $C_{8-22}$ alkyl or alkenyl group and up to 20 ethyleneoxy and/or propyleneoxy groups. Also included are polyoxypropylene/polyethylene oxide copolymers, polyoxybutylenelpolyoxyethylene copolymers and polyoxybutylene/polyoxypropylene copolymers. The polyethoxy, polyoxypropylene and polyoxybutylene compounds may be endcapped with, e.g. benzyl groups to reduce the foaming tendency.

Compositions of our invention may contain amphoteric surfactant.

The amphoteric surfactant may for example be a betaine, e.g. a betaine of the formula: $R_3N^+CH_2COO^-$, wherein each R is an alkyl, cycloalkyl, alkenyl or alkaryl group and preferably at least one, and most preferably not more than one R, has an average of from 8 to 20, e.g. 10 to 18 aliphatic carbon atoms and each other R has an average of from 1 to 4 carbon atoms. Particularly preferred are the quaternary imidazoline betaines of the formula:

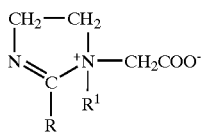

wherein R and R' are alkyl, alkenyl, cycloalkyl, alkaryl or alkanol groups having an average of from 1 to 20 aliphatic carbon atoms and R preferably has an average of from 8 to 20, e.g. 10 to 18 aliphatic carbon atoms and R' preferably has 1 to 4 carbon atoms. Other amphoteric surfactants for use according to our invention include alkyl amine ether sulphates, sulphobetaines and other quaternary amine or quaternised imidazoline sulphonic acids and their salts, and Zwitterionic surfactants, e.g. N-alkyl taurines, carboxylated amido amines such as $RCONH(CH_2)_2N^+$ ($CH_2CH_2CH_3)_2CH_2CO^-_2$, and amino acids having, in each case, hydrocarbon groups capable of conferring surfactant properties (e.g. alkyl, cycloalkyl alkenyl or alkaryl groups having from 8 to 20 aliphatic carbon atoms). Typical examples include 2-tallow alkyl, 1-tallow amido alkyl, 1-carboxymethyl imidazoline and 2 coconut alkyl N-carboxymethyl 2 (hydroxyalkyl) imidazoline. Generally speaking any water soluble amphoteric or Zwitterionic surfactant compound which comprises a hydrophobic portion including $C_{8-20}$ alkyl or alkenyl group and a hydrophilic portion containing an amine or quaternary ammonium group and a carboxylate, sulphate or sulphonic acid group may be used in our invention.

Compositions of our invention may also include cationic surfactants.

The cationic surfactant may for example be an alkylammonium salt having a total of at least 8, usually 10 to 30, e.g. 12 to 24 aliphatic carbon atoms, especially a tri or tetra-alkylammonium salt. Typically alkylammonium surfactants for use according to our invention have one or at most two relatively long aliphatic chains per molecule (e.g. chains having an average of 8 to 20 carbon atoms each, usually 12 to 18 carbon atoms) and two or three relatively short chain alkyl groups having 1 to 4 carbon atoms each, e.g. methyl or ethyl groups, preferably methyl groups. Typical examples include dodecyl trimethyl ammonium salts. Benzalkonium salts having one 8 to 20 C alkyl group two 1 to 4 carbon alkyl groups and a benzyl group are also useful.

Another class of cationic surfactant useful according to our invention comprises N-alkyl pyridinium salts wherein the alkyl group has an average of from 8 to 22, preferably 10 to 20 carbon atoms. Other similarly alkylated heterocyclic salts, such as N-alkyl isoquinolinium salts, may also be used.

Alkylaryl dialkylammonium salts, having an average of from 10 to 30 aliphatic carbon atoms are useful, e.g. those in which the alkylaryl group is an alkyl benzene group having an average of from 8 to 22, preferably 10 to 20 carbon atoms and the other two alkyl groups usually have from 1 to 4 carbon atoms, e.g. methyl groups.

Other classes of cationic surfactant which are of use in our invention include alkyl imidazoline or quaternised imidazoline salts having at least one alkyl group in the molecule with an average of from 8 to 22 preferably 10 to 20 carbon atoms. Typical examples include alkyl methyl hydroxyethyl imidazolinium salts, alkyl benzyl hydroxyethyl imidazolinium salts, and 2 alkyl-1-alkylamidoethyl imidazoline salts.

Another class of cationic surfactant for use according to our invention comprises the amido amines such as those formed by reacting a fatty acid having 2 to 22 carbon atoms or an ester, glyceride or similar amide forming derivative thereof, with a di or poly amine, such as, for example, ethylene diamine or diethylene triamine, in such a proportion as to leave at least one free amine group. Quaternised amido amines may similarly be employed.

Alkyl phosphonium and hydroxyalkyl phosphonium salts having one $C_{8-20}$ alkyl group and three $C_{1-4}$ alkyl or hydroxyalkyl groups may also be used as cationic surfactants in our invention.

Typically the cationic surfactant may be any water soluble compound having a positively ionised group, usually comprising a nitrogen atom, and either one or two alkyl groups each having an average of from 8 to 22 carbon atoms.

The anionic portion of the cationic surfactant may be any anion which confers water solubility, such as formate, acetate, lactate, tartrate, citrate, chloride, nitrate, sulphate or an alkylsulphate ion having up to 4 carbon atoms such as methosulphate. It is preferably not a surface active anion such as a higher alkyl sulphate or organic sulphonate.

Polyfluorinated anionic, nonionic or cationic surfactant may also be useful in the compositions of our invention. Examples of such surfactants are polyfluorinated alkyl sulphates and polyfluorinated quaternary ammonium compounds.

Compositions our invention may contain a semi-polar surfactant such as an amine oxide, e.g. an amine oxide containing one or two (preferably one) $C_{8-22}$ alkyl group, the remaining substituent or substituents being preferably lower alkyl groups, e.g. $C_{1-4}$ alkyl groups or benzyl groups.

Particularly preferred for use according to our invention are surfactants which are effective as wetting agents, typically such surfactants are effective at lowering the surface tension between water and a hydrophobic solid surface. We prefer surfactants which do not stabilise foams to a substantial extent.

Mixtures of two or more of the foregoing surfactants may be used. In particular mixtures of non-ionic surfactants with cationic and/or amphoteric and/or semi polar surfactants or with anionic surfactants may be used. Typically we avoid mixtures of anionic and cationic surfactants, which are often less mutually compatible.

Preferably the THP and the surfactant are present in a relative weight concentration of from 1:1000 to 1000:1, more usually 1:50 to 200:1, typically 1:20 to 100:1, most preferably 1:10 to 50:1, e.g. 1:1 to 20:1 especially 2:1 to 15:1.

Effective doses of the mixture are typically from 0.5 ppm to 2,000 ppm, more usually 2 ppm to 1,000 ppm, e.g. 5 ppm to 500 ppm especially 10 to 250 ppm.

The composition may additionally contain other biocides, water dispersants, antifoams, solvents, scale inhibitors, corrosion inhibitors, oxygen scavengers and/or flocculants.

Our invention includes aqueous solutions containing a biocidally active concentration of a composition of the invention. Such solutions may be water systems or aqueous based products containing functional ingredients as described in GB 2 145 708. Our invention also includes anhydrous, and concentrated aqueous, formulations adapted to provide the aforesaid products on dilution with water.

Scale or corrosion inhibitors which may be added to the water to be treated in conjunction with the present invention include phosphonates, polymaleates, polyacrylates, polymethacrylates, polyphosphates, phosphate esters, soluble zinc salts, nitrite, sulphite, benzoate, tannin, ligninsulphonates, benzotriazoles and mercaptobenzothiazoles all added in conventional amounts. The scale and/or corrosion inhibitors may be added to the water separately from or in association with the phosphonium compound and surfactant. There may be added to the water to be treated oxygen scavengers, flocculants such as polyacrylamide dispersants, antifoams such as silicones or polyethyleneoxylated antifoams or other biocides such as tin compounds or isothiazolones.

The mixture according to our invention may be prepared in situ by adding the THP, the biopenetrant synergist, and optionally the surfactant separately to the water system to be treated. Alternatively and preferably the components may be premixed, either alone, provided that they are miscible in the desired proportions, or with water or other solvents including $C_{1-4}$ monohydric and polyhydric alcohols, ketones. or dispersants such as polyelectrolytes. Typically THP is miscible with cationic surfactants of the quaternary ammonium and phosphonium type, but mixtures with non-ionic surfactants may require dilution with water or solvents.

The microorganisms to be treated are usually bacteria, fungi, yeasts, and algae that grow in aquatic environments,. Included in this classification are sulphate reducing bacteria, e.g. Desulphovibrio, which may occur in oil installations, iron bacteria, e.g. Gallionella and slime forming bacteria, e.g. Pseudomonas, which last are particularly troublesome in aerated aqueous systems.

The water to be treated may be industrial cooling water, e.g. for power stations or chemical plants or for steel or paper or brewing and may be used in closed circuit or in open circuit involving evaporation in cooling towers. Alternatively the water may be process water, especially process water containing significant sources of nutrients for microorganisms such as process water for paper making plants and breweries. Injection water or drilling fluids for oil fields or water produced from oil fields or water used in reverse osmosis plants, e.g. to provide industrial processes or boilers feed water, may be treated.

Other aquatic environments which may be treated with the synergistic biocidal mixtures according to the method for the invention are cooling or process water in board mills. fertiliser manufacture, oil refineries, primary metals manufacture, e.g. steel or copper, petrochemicals, rubber manufacture, textile and fabric industries, industrial gas manufacture, minerals recover, glass and ceramic manufacture, food industry, leather manufacture, heavy and light engineering, including metal fabrication and automotive engineering, furniture manufacture, electronics industry and surface coating and adhesives manufacture and other manufacturing industries.

The process is also applicable to the treatment of geothermal water, water in domestic, industrial and institutional central heating and air conditioning systems and water used for hydrostatic testing of pipelines and vessels, swimming baths and as cooling water for ships and marine engines.

The invention is also applicable to the control of microbial contamination in a wide variety of aqueous based products. For example compositions of the invention may be added to a variety of solutions and emulsion compositions such as paints, cutting oils, bitumen and tar emulsions, adhesives, weedkillers and insecticides, as well as to solid or concentrated compositions for addition to water in the preparation of such products. The invention, therefore, further provides aqueous based products which are subject to microbial spoilage to which has been added a bacteriostatic or bactericidal quantity of a THP salt, a biopenetrant synergist as aforesaid and, optionally, a surfactant. Typically such compositions consist of aqueous solutions, suspensions or emulsions of at least one functional ingredient, together with a minor proportion of a composition of the invention, sufficient to inhibit growth of microorganisms therein.

The systems to which the invention is particularly applicable are those involving the circulation or storage of substantial quantities of water, under conditions favouring the multiplication of bacteria, especially hardy bacteria such as P Aeruginosa, e.g. conditions involving maintaining or periodically raising the water to super ambient temperatures favouring bacterial proliferation, or maintaining nutrients for the bacteria in the water systems.

The invention will be illustrated by the following examples:

EXAMPLE 1

THPS/WSCP mixture was compared with two commercial THP/anionic surfactant products for control of legionella pneumophila.

| METHODOLOGY | |
|---|---|
| Parameter | Details |
| Test medium | Sterile WHO Standard hardness water (total hardness 342 mg liter$^{-1}$) plus 3 mg liter$^{-1}$ iron as ferric sulphate |
| Biocides | Stock solutions 10 x the concentration to be tested Are prepared in WHO standard hardness water |
| pH | 8.0 ± 0.2 |
| pH adjuster | Boric acid/borax buffer as contained in the test Medium |
| Test organism | L. pneumophila sg 1 (NCTC 11192) |
| Test volume | 10 ml |
| Contact temp | 21 ± 1° C. |
| Contact times | 0, 3, 4 and 6 hours |
| Inoculum level | To give an initial concentration of approximately 1 x 10$^5$ cfu/liter |
| Preparation of inoculum | Resuscitate test organism from lyophilised culture. Prepare 48 h plate culture on BCYE agar. Hold at 4° C. overnight. Suspend in 10 ml of test medium. |
| Test method | Add 1 ml of biocide stock solution to 8 ml of test Medium. Control contains 9 ml of test medium only. At time 0 h add 1 ml of inoculum. After the Appropriate contact times remove 1 ml and make serial 10 x dilutions. |
| Enumeration method | By performing Miles and Misra dilution counts onto BCYE agar plates. |

-continued

METHODOLOGY

| Parameter | Details |
|---|---|
| Replication | Spot 33 microliters of each dilution in triplicate onto dry BCYE agar plates to obtain a mean count of surviving legionellae. |
| Plate incubation temperature | 37 ± 1° C. |
| Plate incubation period | 7 days |
| Expression of results | Give number of control and surviving legionellae and the log 10 reduction in numbers of biocide-treated cell suspensions compare to the appropriate controls. |

RESULTS
The results are summarised below

| Product | 3 Hour Contact time | | | 4 Hour Contact Time | | | 6 Hour Contact Time | | |
|---|---|---|---|---|---|---|---|---|---|
| | 25 ppm | 50 ppm | 100 ppm | 25 ppm | 50 ppm | 100 ppm | 25 ppm | 50 ppm | 100 ppm |
| 34% THP 2% anionic surfactant (Comparison A) | $1 \times 10^2$ | $6 \times 10^2$ | $1.6 \times 10^3$ | $1.5 \times 10^2$ | 15 | ND | 30 | ND | ND |
| 74% THP 1% anionic surfactant (Comparison B) | $6 \times 10^4$ | $4.5 \times 10^2$ | ND | $1.4 \times 10^4$ | $6 \times 10^2$ | ND | $4.5 \times 10^2$ | ND | ND |
| 50% active THP/0.7% WSCP (Example) | $3 \times 10^3$ | ND | ND | $5.3 \times 10^2$ | ND | ND | 30.00 | ND | ND |

Notes:
i) ND - Non Detected
ii) The control was $1 \times 10^5$
iii) The following conclusions apply:-
A - Good activity within 4 hours at 50 ppm or above
B - Good activity within 3 hours at 100 ppm or 6 hours at 50 ppm
Example - Good activity within 3 hours at 50 ppm or above The example of the invention also showed superior performance to conventional THP surfactant formulations, to WSCP alone and to THP alone in reducing planktonic bacteria.

The example gave less than half the foaming observed using surfactant containing formulations.

EXAMPLE 2

An aqueous solution comprising 50% THPS and 2% WSCP was added to alginate beads infected with sulphate reducing bacteria When dosed at 250 ppm, solution gave a 100 fold reduction in bacterial counts, compared with a control, after two weeks incubation.

At 500 ppm the solution gave a total kill.

EXAMPLE 3

An aqueous solution comprising 500% THPS and 2% methyl carbitol (diethylene glycol monomethyl ether) was added to alginate beads infected with sulphate reducing bacteria When dosed at 250 ppm, the solution gave a 100 fold reduction in bacterial counts, compared with a control, after two weeks incubation. A mixture of 50% THP and 2% cationic surfactant was inactive at this concentration. At 500 ppm the solution gave a total kill.

The example of the invention also showed superior performance to conventional THP surfactant formulations, to methyl carbitol and to THP alone in controlling both sulphate reducing and planktonic aerobic bacteria.

The example gave less than half the foaming observed using surfactant containing formulations.

The mixture also gives effective control over fungi and algae.

EXAMPLE 4

The alginate bead test of examples 2 and 3 was repeated using sodium naphthalene sulphonatelformaldehyde condensate as the synergist. As 250 ppm the solution gave a 100 fold reduction in bacterial counts after two weeks incubation. At 500 ppm the solution gave a total kill. The volume of foam generated when air was bubbled through the system containing 750 ppm of the active biocidal mixture was half that using THP alone.

EXAMPLE 5

The alginate bead test of Example I was repeated using general heterotroph bacteria and a residence time of two hours. For comparison we used the most commonly used commercial THP biocide product which is an aqueous solution comprising 50% THPS and 2% of an anionic surfactant available commercially under the Registered Trade Mark "DOWFAX" 2A1.

Various mixtures each comprising 50% THPS and 2% of biopenetrant were compared at 250 ppm and at 125 ppm dosage. The log reduction in bacterial counts is given in the table.

TABLE

| BIOPENETRANT | FUNCTIONALITY | LOG REDUCTION |
|---|---|---|
| Comparative | Surfactant | |
| 250 ppm | | 3.7 |
| 125 ppm | | 3.0 |
| Sodium xylene sulphonate | Hydrotrope | |
| 250 ppm | | 4.7 |
| 125 ppm | | 2.7 |
| THP a condensate | "Syntan" | |
| 250 ppm | | 5.00 |
| 125 ppm | | 3.70 |
| Formaldehyde/dihydroxy-phenylsulphono poly condensate | "Syntan" | |
| 250 ppm | | 4.0 |
| 125 ppm | | 2.7 |
| Urea | | |

TABLE-continued

| BIOPENETRANT | FUNCTIONALITY | LOG REDUCTION |
|---|---|---|
| 250 ppm | Hydrotrope | 6.7 |
| 125 ppm | | 4.0 |

In each case the biopenetrant of the invention showed improved biocidal activity compared with the surfactant in the comparative example, and gave substantially less foaming.

EXAMPLE 6

The comparative formulation of Example 5 was compared with a mixture of 50% THPS, 1% surfactant and 1% diethylene glycol monomethyl ether. The mixture gave greater log reductions than either the comparative formulation or the formulation of Example 3.

What is claimed is:

1. A biocidally synergistic mixture comprising THP and at least one THP-compatible non-surfactant biopenetrant wherein said biopenetrant is a polymer or copolymer, having a plurality of quaternary ammonium groups, and the concentration of THP is from 10 to 75% by weight and the concentration of biopenetrant is from 0.1 to 10% by weight.

2. A composition according to claim 1 wherein said biopenetrant is a compound having a polymeric cation with a formula

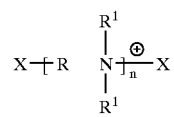

wherein each R is a divalent organic group constituting, with the ammonium group, a monomeric residue, or is separately selected from two or more comonomeric residues and each $R^1$ is an alkyl or hydroxyalkyl group, X is hydrogen or a monovalent inorganic or organic end capping unit and n is from 2 to 3000.

3. A composition according to claim 1 consisting of an aqueous solution wherein the concentration of THP is from 30 to 50% by weight of the solution and the concentration of non-surfactant biopenetrant synergist is from 0.5 to 2% by weight of the solution.

4. A composition according to claim 1 additionally comprising a surfactant.

5. A composition according to claim 4 wherein the surfactant is present in a weight proportion of from 50:1 to 1:200 based on the weight of the THP.

6. A method for treating aqueous systems to inhibit or destroy microbial contamination, which comprises adding thereto, together or separately, a biocidally synergistic amount of THP, at least one THP-compatible non-surfactant biopenetrant and, optionally, a surfactant, wherein said biopenetrant comprises a polymer or copolymer, having a plurality of quaternary ammonium groups and the concentration of THP is from 10 to 75% by weight and the concentration of biopenetrant is from 0.1 to 10% by weight.

* * * * *